United States Patent [19]

Ohlson

[11] Patent Number: 5,764,724
[45] Date of Patent: Jun. 9, 1998

[54] METHOD OF MAKING X-RAY PHOTOGRAPHS OR EXPOSURES OR OTHER TYPE OF RADIATION SENSORING, SUCH AS ELECTRONIC IMAGE STORAGE, AND A PATIENT TABLE HAVING A RECEPTOR UNIT FOR SUCH PHOTOGRAPHY, EXPOSURE OR IMAGE STORAGE

[75] Inventor: Carl-Eric Ohlson, Stockholm, Sweden

[73] Assignee: AO Medical Products AB, Stockholm, Sweden

[21] Appl. No.: 776,392

[22] PCT Filed: Jul. 26, 1995

[86] PCT No.: PCT/SE95/00887

§ 371 Date: Jan. 28, 1997

§ 102(e) Date: Jan. 28, 1997

[87] PCT Pub. No.: WO96/03077

PCT Pub. Date: Feb. 8, 1996

[30] Foreign Application Priority Data

Jul. 28, 1994 [SE] Sweden ................... 9402589

[51] Int. Cl.[6] .................................... G03B 42/04
[52] U.S. Cl. .................. 378/177; 378/167; 378/175
[58] Field of Search .................... 378/177, 167, 378/175, 169, 170, 178, 179, 181, 208, 209, 187

[56] References Cited

U.S. PATENT DOCUMENTS

| 4,468,803 | 8/1984 | Ronci | 378/181 |
| 5,023,899 | 6/1991 | Ohlson | 378/177 |
| 5,157,707 | 10/1992 | Ohlson | 378/181 |

FOREIGN PATENT DOCUMENTS

463237 B  10/1990  Sweden.

*Primary Examiner*—Don Wong
*Attorney, Agent, or Firm*—Sughrue, Mion, Zinn, Macpeak & Seas, PLLC

[57] ABSTRACT

A method of X-ray photography or a method of some other type of radiation sensoring, such as electronic image storage, employs the use of a receptor unit (2) which can be swung outwards and upwards from an initial position in or beneath a patient support table (1) about alternative pivot centers (11, 12) disposed in the region of respective side edges of the table to alternative positions for operating with a horizontal beam path. The receptor unit can be swung out about a vertical axis from these positions in which it is parallel with the longitudinal direction of the table to a position in which it is parallel with the longitudinal direction of the table to a position in which the unit is perpendicular to the longitudinal axis of the table, to enable pictures to be taken of a patient seated in a wheelchair, for instance. The invention also relates to a patient support table (1) provided with a receptor unit (2) of this kind.

19 Claims, 9 Drawing Sheets

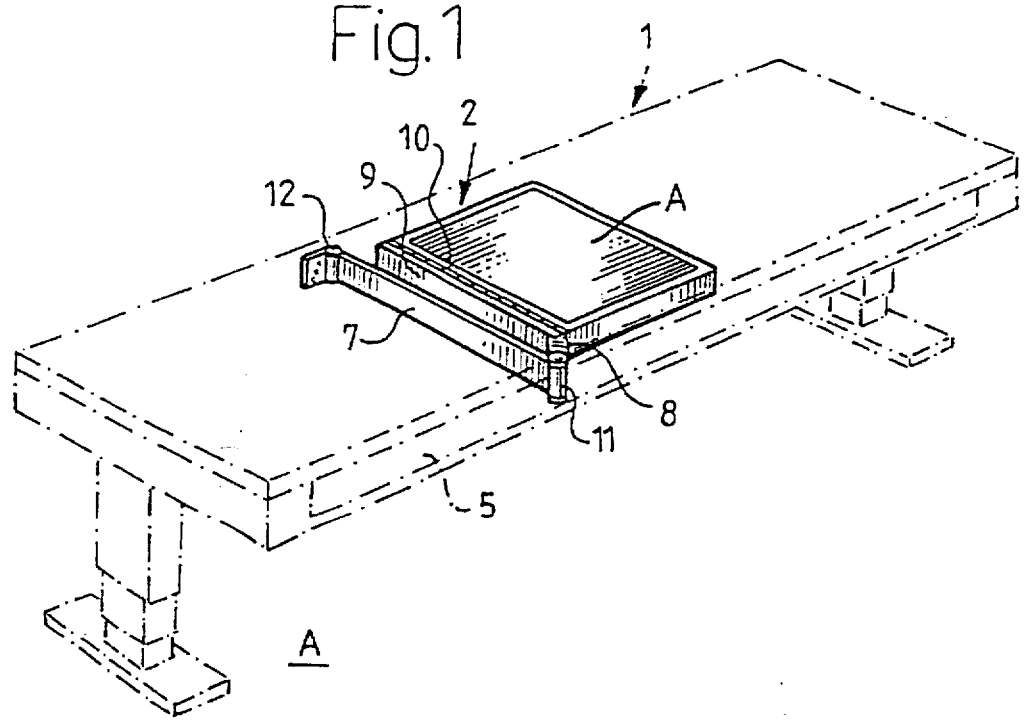
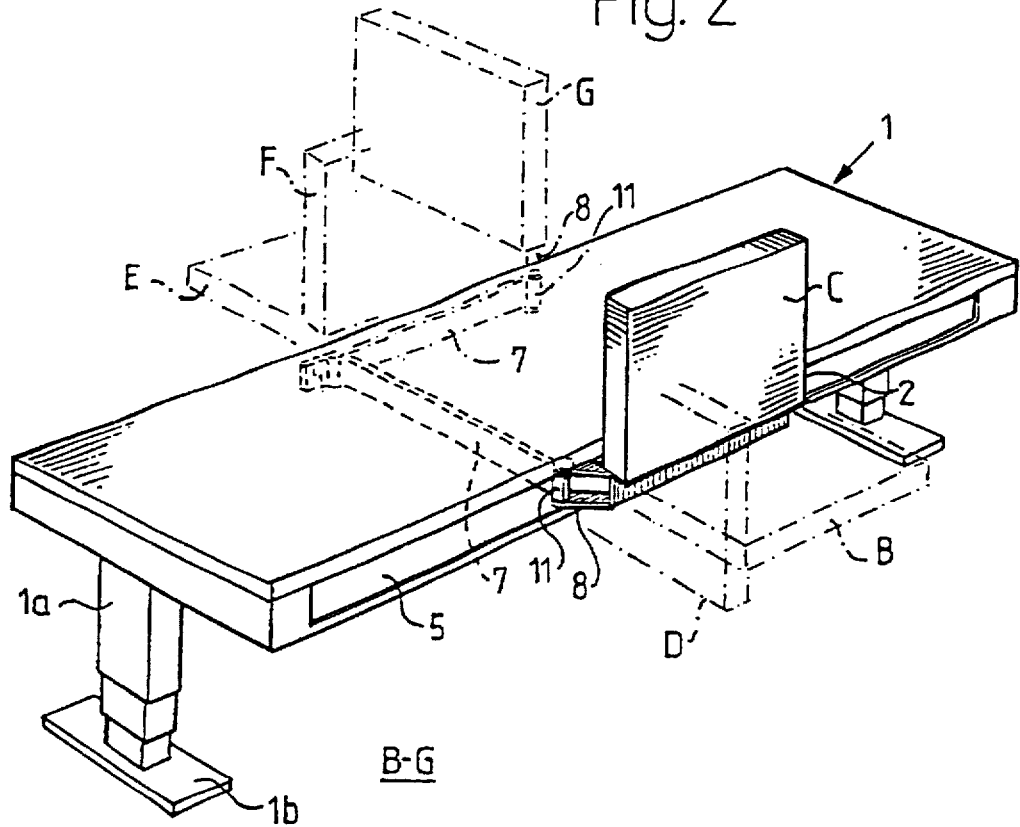

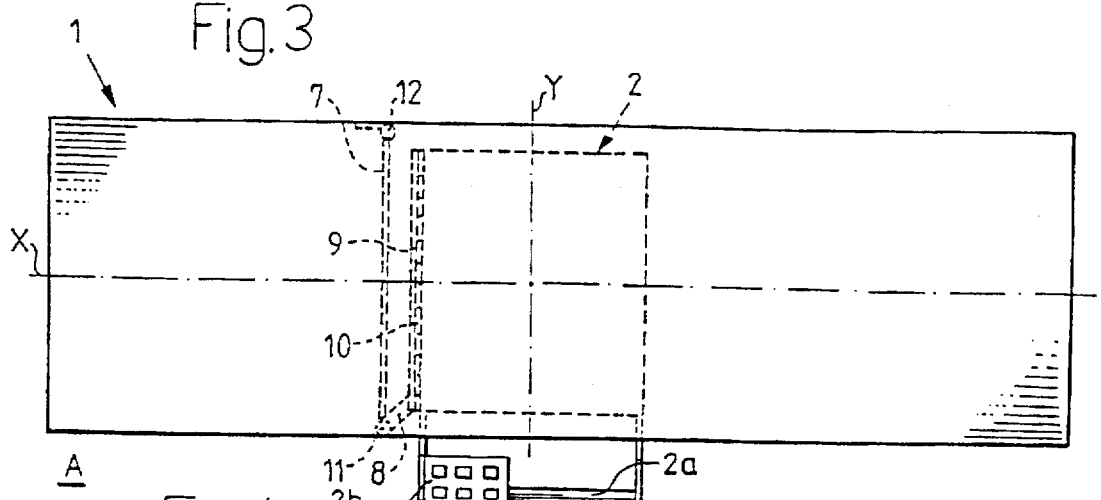
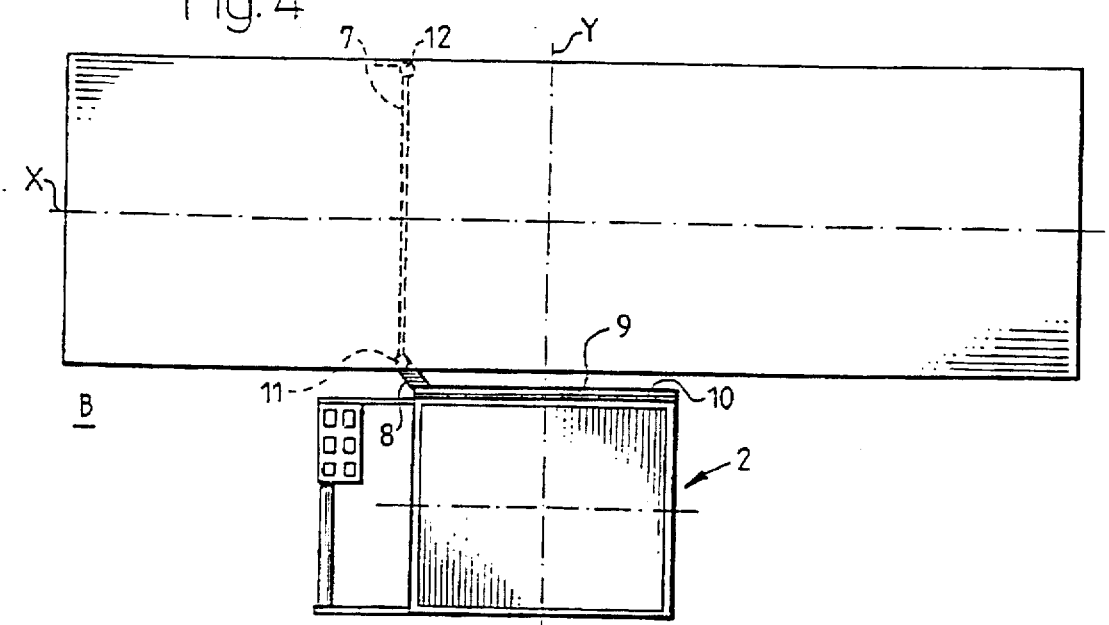
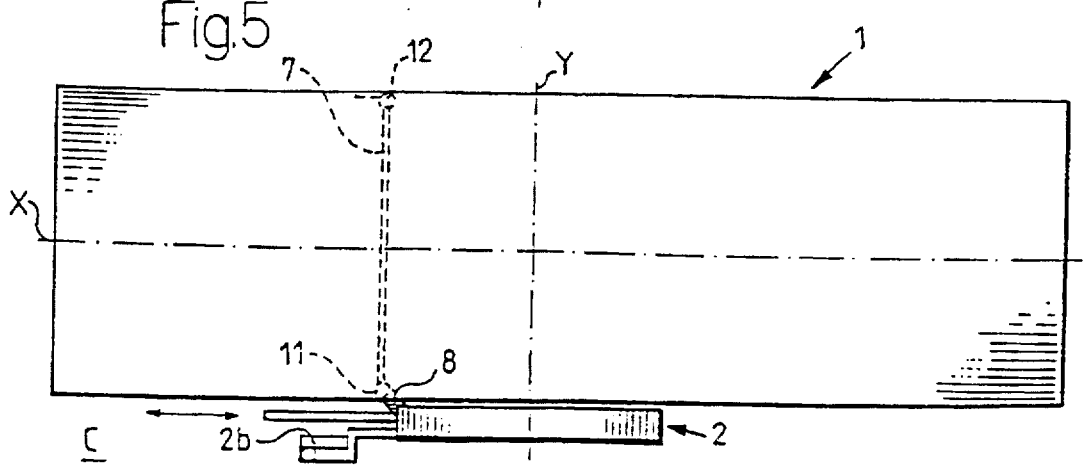

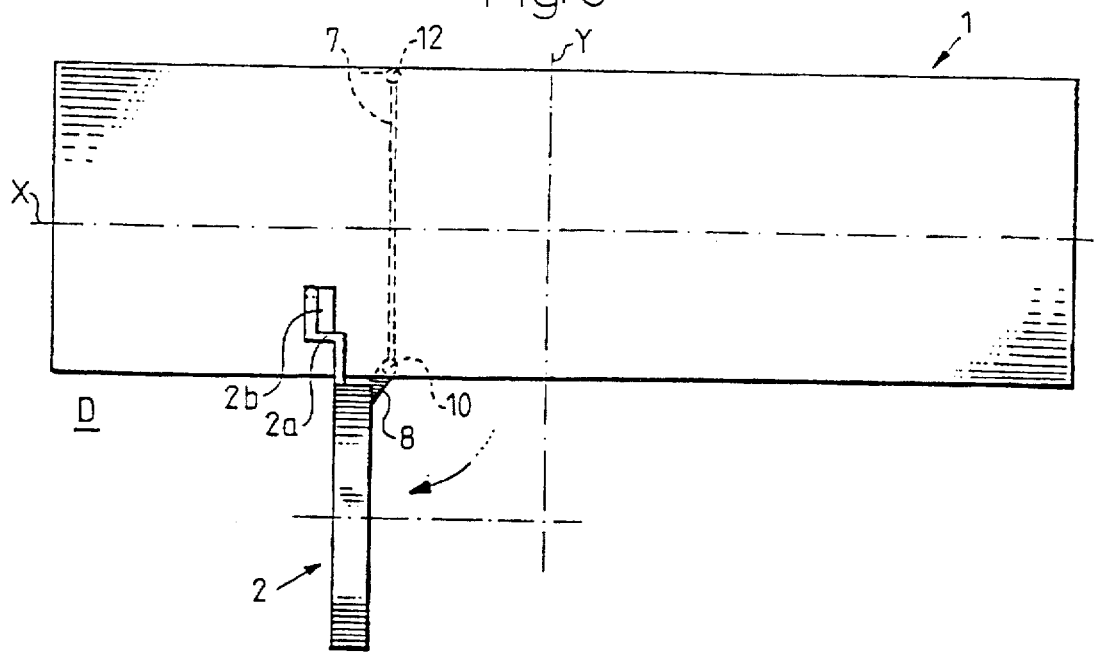
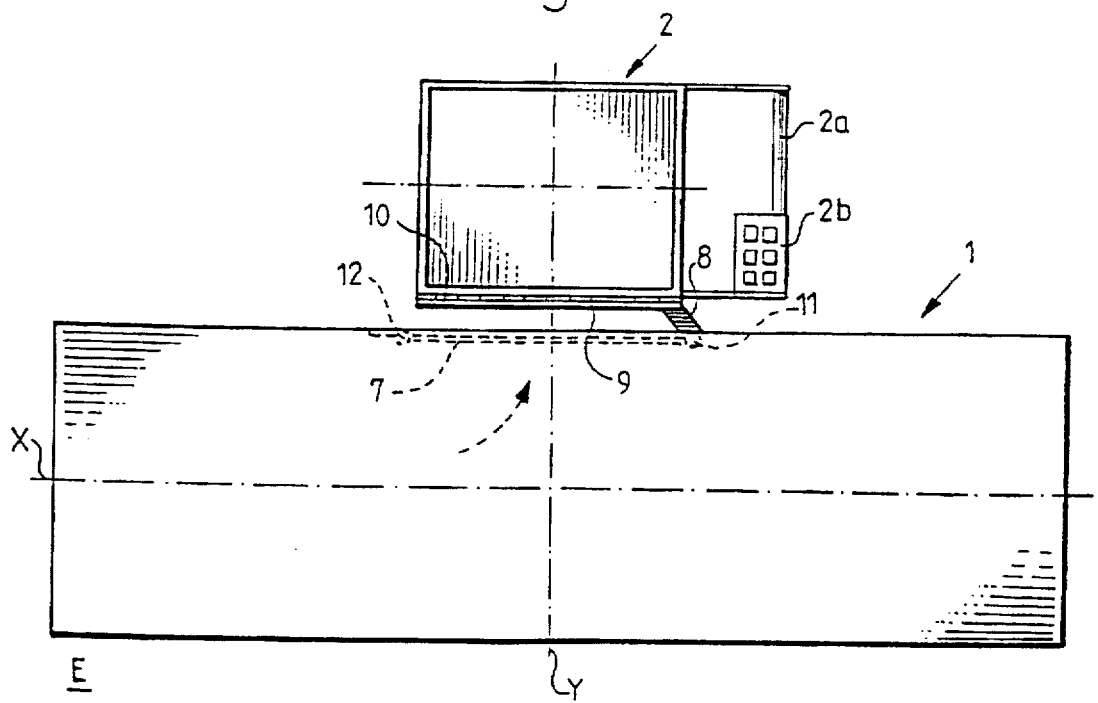

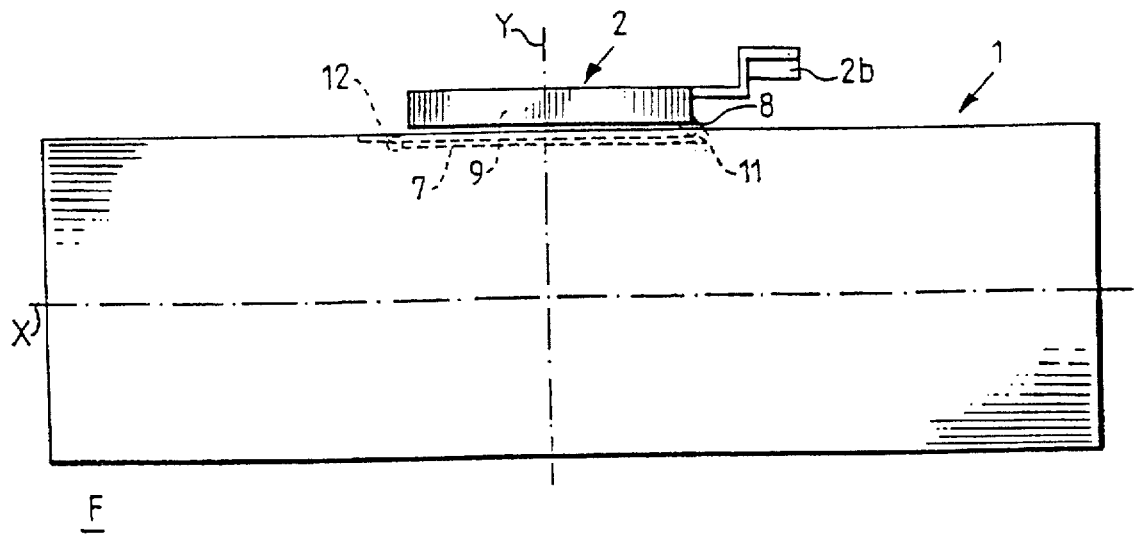
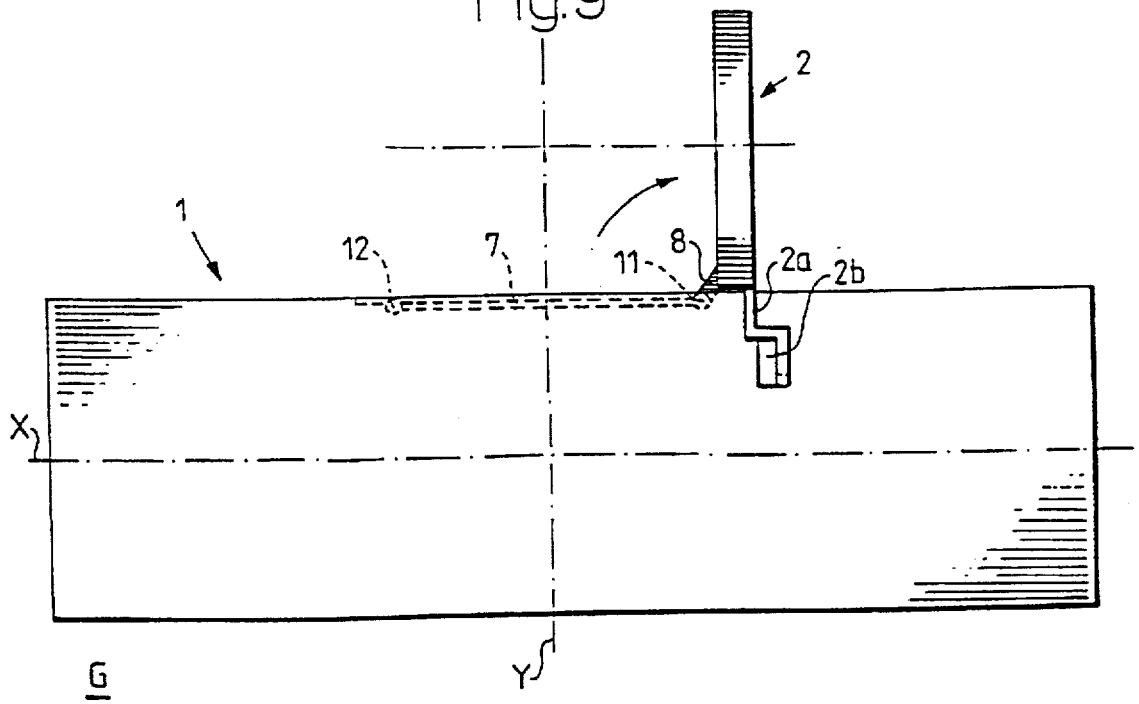

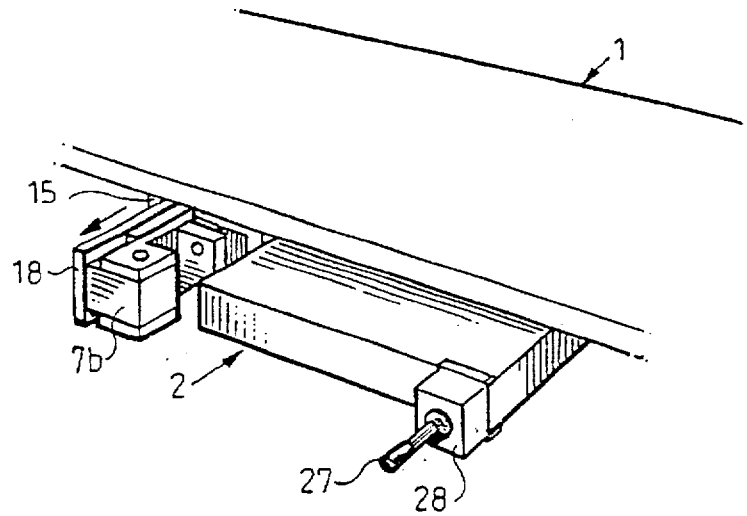
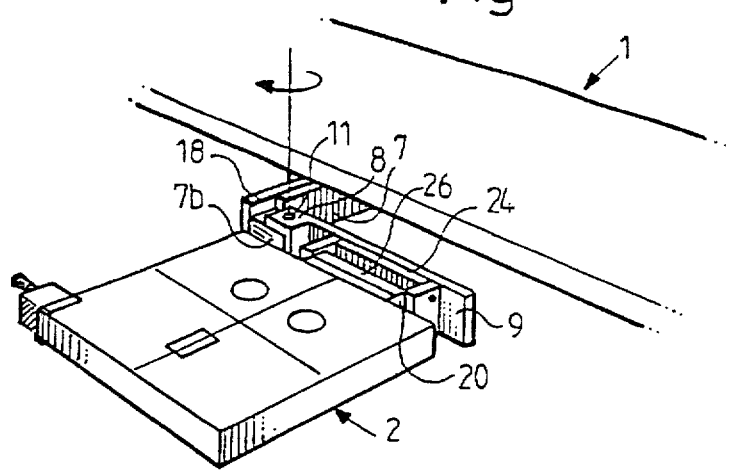
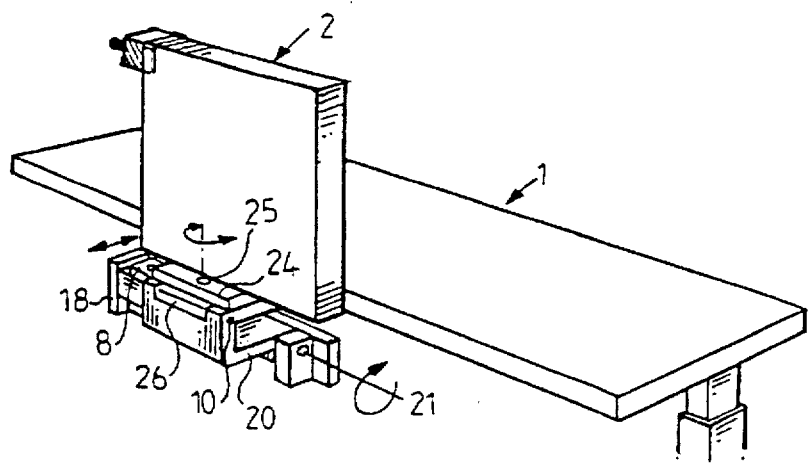

METHOD OF MAKING X-RAY PHOTOGRAPHS OR EXPOSURES OR OTHER TYPE OF RADIATION SENSORING, SUCH AS ELECTRONIC IMAGE STORAGE, AND A PATIENT TABLE HAVING A RECEPTOR UNIT FOR SUCH PHOTOGRAPHY, EXPOSURE OR IMAGE STORAGE

TECHNICAL FIELD

The present invention relates to a method of imaging a person or an object in at least two directions by X-ray photography, while using an X-ray cassette as a receptor or other forms of radiation-absorbing techniques with the aid of a radiation receptor, for instance for electronic image storage.

In imaging processes of this kind, there is used a radiation source which is supported for movement in X-, Y- and Z-directions and which is rotatable about a horizontal axis. The receptor unit may be mounted in or positioned beneath a patient table and is movable in the X-direction. Movement of the radiation source may be initiated automatically, as the receptor unit is moved.

By X-direction is meant here and in the following a direction of movement which is parallel with one long side of the patient table, while by Y-direction is meant a direction of movement perpendicular to the extension of said long side, i.e. a direction of movement parallel with the short sides of the table. By Z-direction is meant movement in a vertical direction. This enables the patient table to be brought to different positions in relation to a tower column or a ceiling-mounted tower which carries the beam source.

The present invention also relates to a patient table equipped with a receptor unit, and more specifically to a patient table of the kind defined in the preamble of claim 5.

BACKGROUND PRIOR ART

GB-B-1,323,769 (Picker Corp.) describes apparatus comprising a receptor part disposed in a patient support table, and an overlying ceiling-mounted beam source. The apparatus enables side-on photographs to be taken with a horizontal beam path, by swinging-up the patient's support table about a horizontal axis and pivoting the beam source. The apparatus also enables the image size and the shutter setting to be varied in relation to the beam-source/receptor distance ("SID", i.e. "source-image-distance". However, movement of the beam source and swinging of the patient support table must be effected manually, which is experienced as troublesome by the radiologists concerned.

EP-A-0 430 934 (AO Medical Products) describes a method of the aforesaid kind in which activation of a secondary receptor pivotally associated with the receptor unit or mountable thereon and extending in a vertical plane results, optionally after a time delay, in automatic movement of the beam source to a basic setting for horizontal, centered beam path onto the secondary receptor.

A Philips brochure describes a patient support table which carries a receptor unit for a vertical beam path. This receptor unit can be swung outwards and upwards from one side of the table, to a position for receiving a horizontal beam path.

This latter arrangement, which is considered to represent the nearest prior art, has a number of drawbacks. When the receptor unit is to be swung out and up to receive a horizontal beam path, it is necessary for personnel who need to stand on the other side of the table in order to manoeuver the beam source to move around the table to swing the receptor unit outwards and upwards, and then move back around the table and place themselves in their original position in which the beam source can be manoeuvered. This procedure is experienced by the personnel as being both troublesome and time-consuming. The described solution also has other drawbacks from an ergometric aspect.

Another drawback is that the receptor unit is not centred in relation to the beam path when swung outwards and upwards from the table, and it is therefore necessary to move the beam source in the X-direction when adjusting for horizontal beam path.

Furthermore, this known arrangement only allows an exposure to be taken from one side of the patient. It is often difficult to "turn" the patient, particularly when the patient is seriously injured.

The effect of these drawbacks may sometimes be so serious as to impair the clarity of the pictures to an extent such as to require the X-ray to be taken again, therewith exposing the patient to an unnecessarily high radiation dosage.

THE OBJECTS OF THE INVENTION

One object of the invention is to provide a method and a patient support table of the aforedefined kind which, with one and the same receptor equipment, enables pictures to be taken with a vertical beam path, for instance with the patient lying down, and also with a horizontal beam path from each side of the patient support table, and preferably without changing the setting of the beam source in the X-direction, i.e. without moving the beam source laterally.

Another object is to provide equipment of the aforesaid kind which is superior to earlier known equipment with regard to ergometrics.

A further object of the invention is to provide equipment which can be adapted readily to different specific parameters, such as receptor size, table width, etc.

BRIEF DESCRIPTION OF THE INVENTION

These and other objects are fulfilled with a method of the kind defined in the preamble of claim 1 and having the features set forth in the characterizing clause of said Claim.

The invention enables the beam to be kept central in the Y-direction in the transition between a vertical and a horizontal beam path, irrespective of the alignment of the horizontal beam path in the Y-direction. In addition, the invention enables a receptor that has been swung up to a position above the table to be moved towards the patient and therewith obtain optimum picture sharpness and therewith a clearer diagnosis from the picture or image obtained.

The invention also enables the positions of pivot centres to be determined accurately in accordance with the different parameters that apply in individual cases, for instance in accordance with the dimensions of the receptor unit, the width of the patient support table, the desire for the bottom edge of the receptor to be located at a given height above the table when the receptor is in an outwardly swung position, and so on.

The present invention also enables the introduction of mutually dependent locking facilities with a crosswise function for outward swinging of the receptor unit in the horizontal plane. The effect afforded by the invention can be likened to the hinge of a hinged door, i.e. the receptor can present alternative pivot centres in dependence on the direction in which the receptor unit is swung outwards. Left and right pivot centres can be readily adapted to occurrent types of tables.

In practice, it is preferred that respective pivot centres are so placed in the X- and Y-directions that centering of the beam source in the X-direction will be the same for both a horizontal and a vertical beam path. A preferred method according to the invention is characterized by swinging the receptor unit in one or both of the alternative outwardly and upwardly swung positions to a position in which the unit is perpendicular to the longitudinal axis of the table, therewith enabling X-ray pictures to be taken of a patient seated in a wheelchair, for instance.

This enables the requirement of a separate frame or stand for taking such pictures to be dispensed with. This special outwardly swung position of the receptor unit may also be used in other circumstances, for instance when taking lung X-rays, etc.

In one preferred method of applying the invention, the receptor unit is movable in the X-direction along the longitudinal axis of the table with corresponding automatic movement of the beam source and resetting of said source for a horizontal beam path towards the receptor unit, after having swung the receptor unit outwardly and upwardly beyond a side edge of the table.

Thus, in the case of this preferred method of application, the beam source is adjusted automatically to the position adopted by the receptor unit.

In accordance with one method of application, the receptor unit is supported by a carriage which can move in the X-direction relative to the table and which can also be moved in the Y-direction relative to the carriage. The unit is carried by arms whose lengths can be adjusted and which supports the unit stably and reliably.

In this method of application, the receptor unit can be dropped down or raised up from an outwardly swung horizontal position on each side of the table, to a respective vertical position beneath or above the table, by pivotal movement about mutually parallel axles located at different levels.

When in an outwardly swung and upwardly lifted vertical position, the receptor unit can be swung about a central, vertical axle for work with an angled beam path.

According to another aspect, the invention also relates to a patient support table provided with a receptor unit and intended for X-ray photography or X-ray exposure or some other type of beam sensing, e.g. electronic image storage, said patient support table being characterized essentially by the features set forth in the following claims 8–16.

BRIEF DESCRIPTION OF THE DRAWINGS

The invention will now be described in more detail with reference to exemplifying embodiments thereof and also with reference to the accompanying drawings, in which FIG. 1 is a perspective view of a receptor unit which can be swung outwardly and upwardly in different directions in accordance with the invention and which is mounted on a patient support table shown in chain lines;

FIG. 2 is a perspective view of the patient support table shown in FIG. 1 with the receptor unit in an outwardly and upwardly swung position, referenced C, to the right of the patient table, wherein the Figure also shows a number of possible alternative positions of the receptor unit, referenced B, D, E, F and G respectively, wherein the initial position shown in FIG. 1 is referenced A;

FIGS. 3–9 show the patient support table from above with respective receptor units in the aforesaid different positions, wherein FIG. 3 corresponds to positions A, FIG. 4 corresponds to position B, FIG. 5 corresponds to position C, FIG. 6 corresponds to position D, FIG. 7 corresponds to position E, FIG. 8 corresponds to position F and FIG. 9 corresponds to position G;

FIG. 14 is a perspective view of the table and the carriage-supported receptor unit in a position in which the unit lies partially outside the table, i.e. prior to swinging the receptor unit outwards;

FIG. 15 is a perspective view corresponding to the view of FIG. 14 and shows the receptor unit swung out away from the table;

FIG. 16 is a perspective view corresponding to the view of FIG. 15 but showing the receptor unit swung to a vertical position;

DESCRIPTION OF PREFERRED EMBODIMENTS

Figure 10:
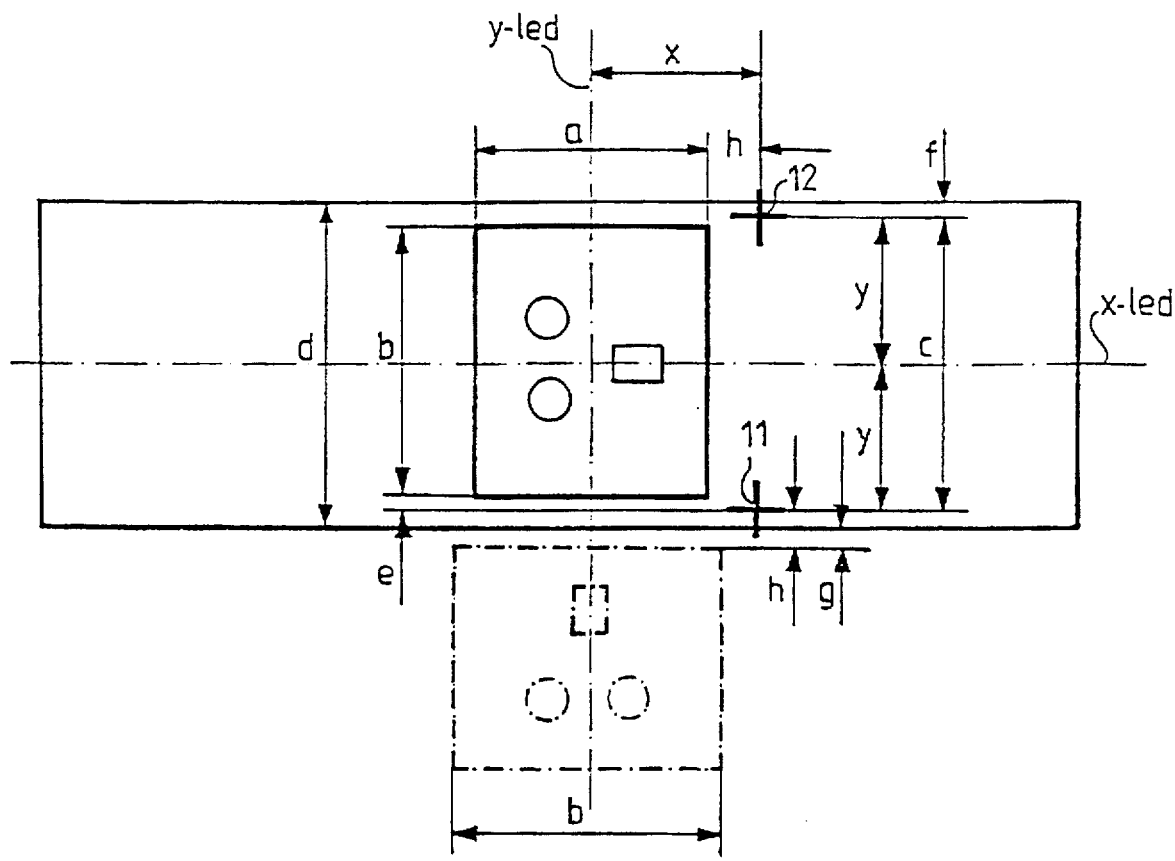
FIG. 10 is a view of the patient support table shown in the other Figures from above, with the receptor unit shown in positions A and B, wherein the Figure also shows a number of reference signs relating to different relevant measurements and distances regarding the patient support table and the receptor unit respectively as explained in more detail below, and wherein the figure thus illustrates the geometric relationship between occurrent magnitudes.

The reference numeral 1 used in the various Figures identifies a patient support table for use in X-ray photography or in some other type of beam sensing, such as electronic image storage, for instance. The patient support table is supported on telescopic legs 1a provided with floor plates 1b, which enable the table to be adjusted vertically.

The table includes a recess or aperture 5 for the accommodation of a receptor unit, generally referenced 2. The receptor unit can be moved in the X-direction, i.e. in the longitudinal direction of the table. Some of the FIGS. 3–9 show an X-axle in the centre of the table. To this end, the receptor unit may be mounted on a carriage or like device (not shown) mounted in the table.

The receptor unit 2 is intended for coaction with a beam source (not shown) which can be moved in the X-direction, the Y-direction, i.e. transversely to the long axis of the table, and in the Z-direction, i.e. in a vertical direction. The beam source can also be swung about a horizontal axle.

The receptor unit 2 is supported by arms 7, 9 which are joined together via a link 8 and which coact with pivot centres 11, 12 having vertical pivot axles located in the region of each side edge of the table, such as to enable the receptor unit to be swung out to alternative positions on each side of the table. The arm 9 is connected to the receptor unit 2 by means of a horizontal hinge 10. The receptor unit 2 can thus be swung out from the initial position A shown in FIG. 1 to the position B shown in FIG. 2, this latter position also being shown in FIG. 4.

The receptor unit shown in FIGS. 3–9 correspond to the receptor unit shown in FIGS. 1 and 2, with the exception that the units shown in FIGS. 3–9 have a handgrip 2a which enables the receptor unit to be swung manually. The receptor units are also provided with an operating panel 2b having push buttons by means of which different receptor locking and receptor release operations can be initiated, the beam source activated, etc.

The receptor can be swung up about the horizontal hinge 9 from the position B shown in FIG. 4 to the position C shown in full lines in FIGS. 2 and 5.

The vertical axle 11 enables the receptor unit to be swung from position C to a position D, shown in FIG. 6, in which the receptor unit is at right angles to the table 1. With the receptor unit in position D, side-on pictures and front-on pictures can be taken of a patient seated in a wheelchair, for instance.

In FIG. 7, the receptor unit 2 has been swung from the initial position shown in FIGS. 1 and 3 in the other direction, about the vertical axle 12, to the position E in which the receptor unit is located slightly outside the opposing side edge of the table. It will be seen that in this position the receptor unit is also centered in the X-direction, i.e. there is no need to move the beam source laterally.

The receptor unit can be swung up from the position E shown in FIG. 7 to the position F shown in FIG. 8.

FIG. 9 illustrates the receptor unit swung from position F to position G, this position corresponding to the position D on the other side of the table.

two pivot centres 11 and 12 can be determined as desired, in a manner described in more detail below.

The pivot axle about which the receptor unit is swung up is placed so that when the unit is in an upwardly swung position, the bottom edge of the unit will be located roughly in the plane of the table top or above the table top, for instance at a distance of 20 mm therefrom.

One advantage is that the operating unit 2a, 2b is located on the same side of the table as the radiologist or his/her assistant, therewith facilitating operation.

Figure 11:
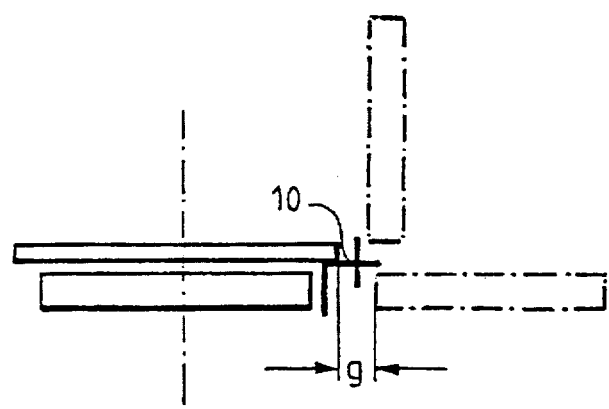
FIG. 11 is a side view illustrating different receptor positions.
Figure 12:
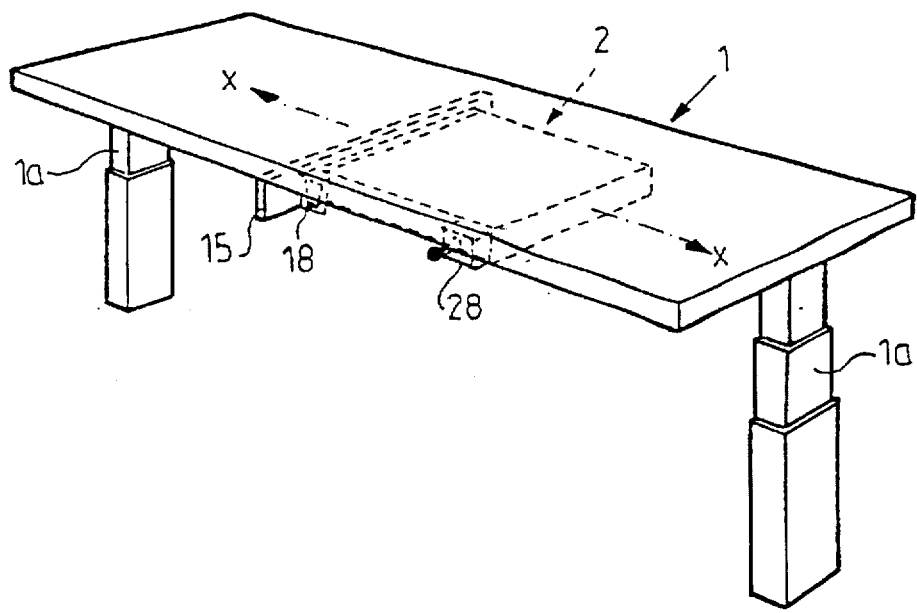
FIG. 12 is a simplified principle perspective view of a modified design of the patient support table, in which the receptor unit is accommodated in a carriage which can be moved along the table in the X-direction and is so mounted in the carriage as to be also movable in the Y-direction.
Figure 13:
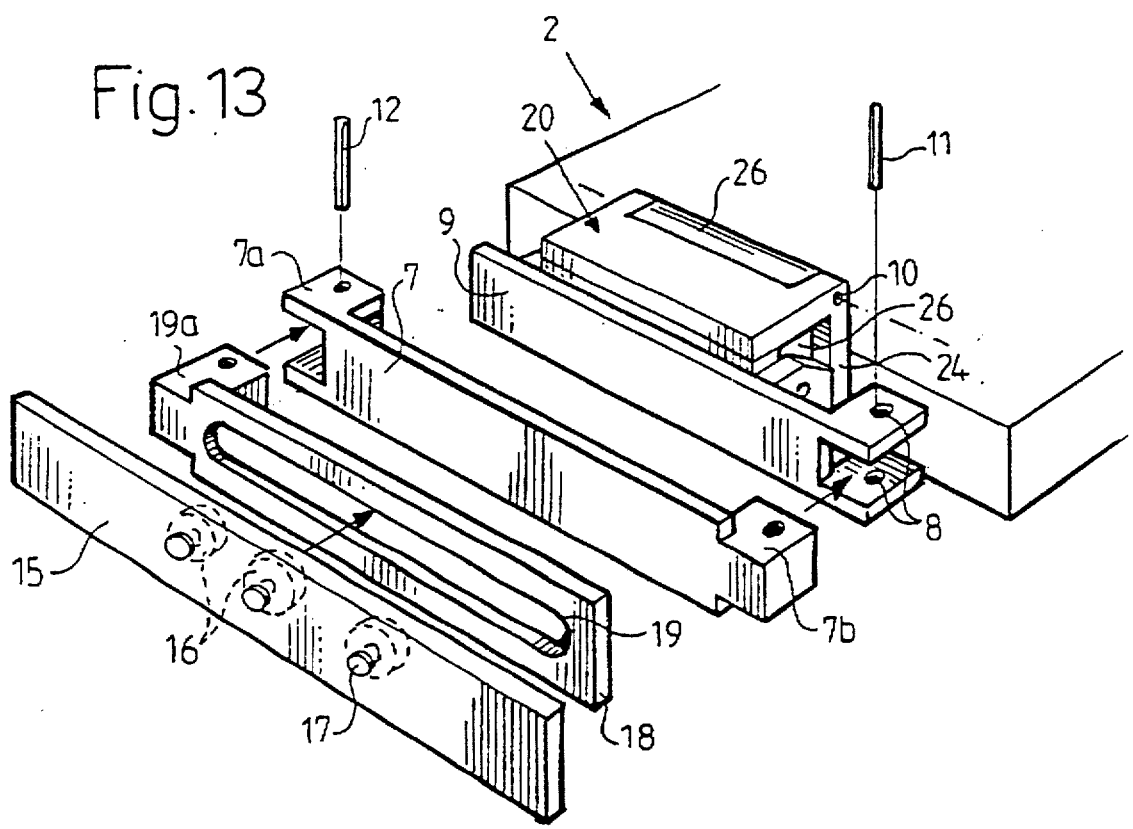
FIG. 13 is a perspective exploded view illustrating some of the elements by means of which the receptor unit is supported by the carriage for movement in the Y-direction.

FIGS. 10 and 11 illustrate different conceivable component measurements and the distances therebetween. The measurements also correspond to a left-hung receptor unit. In the initial position of the receptor unit a) is the width of the receptor unit in the X-direction;

b) is the length of the unit in the Y-direction;

c) is the distance between the two pivot centres 11 and 12;

d) is the width of the table;

e) is the distance in the Y-direction between the receptor unit and the pivot centre 11;

f) is the distance between one side edge of the table and the pivot centre 12;

g) is the distance in the Y-direction between the opposite side edge of the table and one end edge of the receptor unit in position B;

h) is the distance between this last-mentioned side edge and the pivot centre 11;

x) is the distance in the X-direction between the centre point of the receptor unit in position A and the pivot centres 11, 12;

y) is the distance in the Y-direction between the centre point of the receptor unit in position A and the pivot centres 11, 12; and h) is a radius corresponding to the length of the link 8.

The following relationships will thus apply:

$x = Y = z/2$
$e = (c-b)/2$
$f = (d-c)/2$
$g = (2 \times c - a - d)/2$
$h = (c-a)/2$ Table 1 below lists measurements which can be applied and calculated with regard to a constructional design preferred in practice.

TABLE 1

| Receptor width a | Receptor depth b | Variable Axle distance c | Table width d | Distance centre Receptor e | Variable Centre Receptor f | Receptor Plate g | Center Receptor h |
|---|---|---|---|---|---|---|---|
| 479 | 580 | 590 | 700 | 20 | 55 | 1 | 56 |
| 564 | 580 | 590 | 700 | 20 | 55 | −42 | 13 |
| 479 | 580 | 600 | 700 | 40 | 50 | 11 | 61 |
| 564 | 580 | 600 | 700 | 40 | 50 | −32 | 18 |
| 479 | 580 | 610 | 700 | 60 | 45 | 21 | 66 |
| 564 | 580 | 610 | 700 | 60 | 45 | −22 | 23 |

The various Figures illustrate that when applying the inventive method, the beam can be kept centered in the X-direction in the transition between the vertical beam direction and the two horizontal beam directions, in accordance with the position shown in FIGS. 1 and 2 and in FIGS. 7 and 8 respectively. At the same time, the positions of the The Table shows the aforesaid relationships in one application example, in which c and f are variables.

FIGS. 12–19 show a modified design of the receptor unit 2, to-wit a design in which the receptor unit is carried for movement in the Y-direction by an element 15 which may either be part of a carriage which can be moved in the X-direction in relation to the Table 1 or form part of a stand or frame that is fixed in relation to the table.

In the case of the illustrated embodiment, the element 15 includes three rollers 16 which are carried for rotation on three horizontal axles 17 and which are disposed in an elongated slot 19 provided in a further element 18 and functioning to guide movement of the further element 18 in relation to the first-mentioned element 15.

The further element 19 is provided at one end with a bearing block 19a which coacts with a corresponding bearing block 7a on a corresponding end of the arm 7. The arm 7 of this embodiment is thus journalled more stably about the axle 12 than in the aforedescribed embodiments.

The other end of the arm 7 includes a bearing block 7b which coacts with a bearing element 8 corresponding to the bearing element 7a on the arm 7, this arrangement corresponding functionally to the link element 8 of the aforedescribed embodiments. The journal axle of this embodiment is referenced 11, as in the former cases.

For the purpose of supporting the receptor unit 2, the arm 9 is firmly secured with the aid of an intermediate element 6 which is embraced by a U-shaped block 20 which is connected to the intermediate element 26 in a manner to allow the block 20 to pivot about the horizontal axle 10. As will be seen from FIGS. 14–16, the receptor unit carried by the carrier and guide arrangement 15–19 can be displaced in the Y-direction relative to the element 15 to the position shown in FIG. 15 in which the receptor unit 2 lies outside the confines of the Table 1. The receptor unit can then be swung up to the vertical position shown in FIG. 16 about the axle 10.

Figure 17:
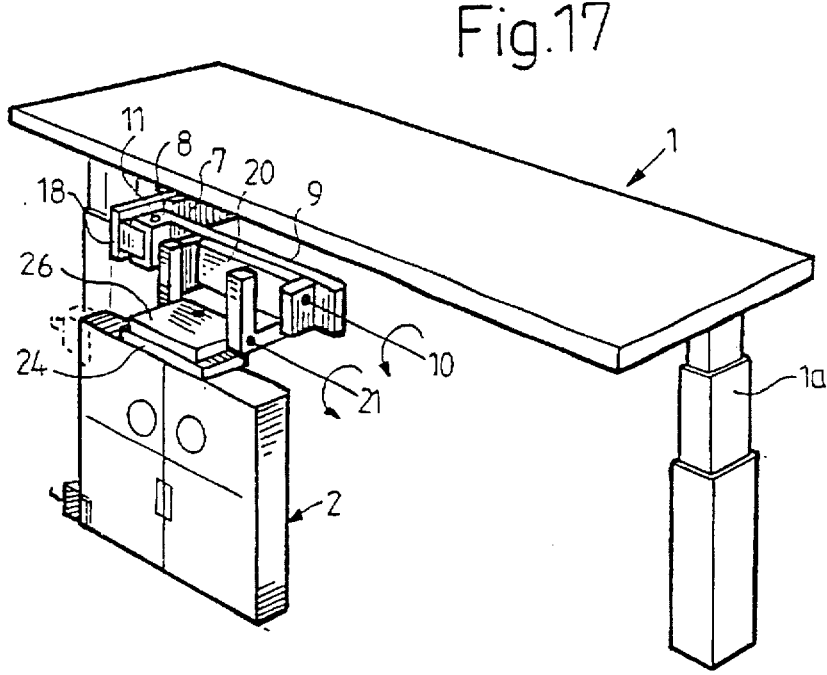
FIG. 17 is a perspective view of the arrangement shown in FIGS. 12–16, wherein the receptor unit has been swung down to a vertical position about an axle which is parallel with the axle used to swing-up the unit, this downwardly swung position being used, for instance, to take X-rays of the knees of a seated patient.

In FIG. 17, the receptor unit 2 is shown to be swung down to a vertical position which defines an angle of 180° with the position shown in FIG. 16. X-rays can be taken of the knees of a standing or sitting patient with the receptor unit in this position.

The receptor unit 2 is swung down around the axle 21, which is parallel with the axle 10 but located on a lower level than said axle.

The intermediate element 26 supports the receptor unit 2 through the medium of a plate 24. As will be seen from FIG. 16, the plate 24 is pivotal about a vertical axle 25. The receptor unit 2 accompanies the movement of plate 24 as it swings around the vertical axle 25, therewith enabling the receptor unit to be moved to the position shown in FIG. 19, for instance. In this position, the receptor unit is able to take pictures with an angled beam path.

Figure 18:
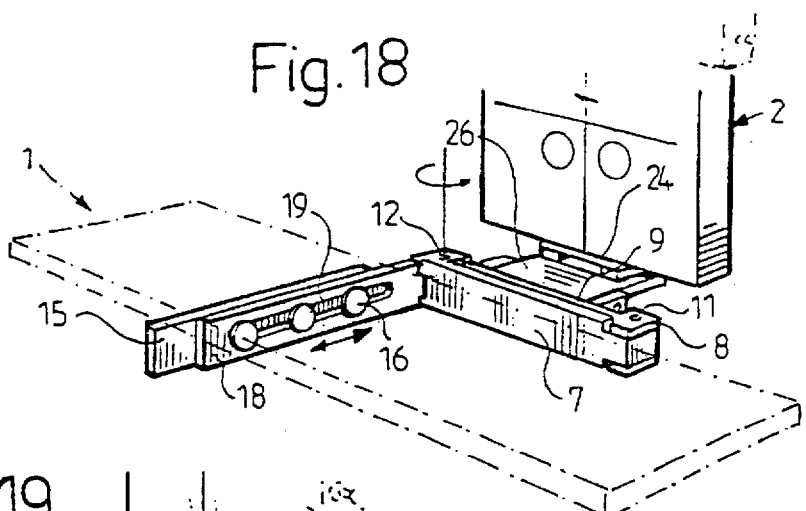
FIG. 18 is a perspective view of parts of those elements which function in the linear and pivotal movements of the receptor unit.
Figure 19:
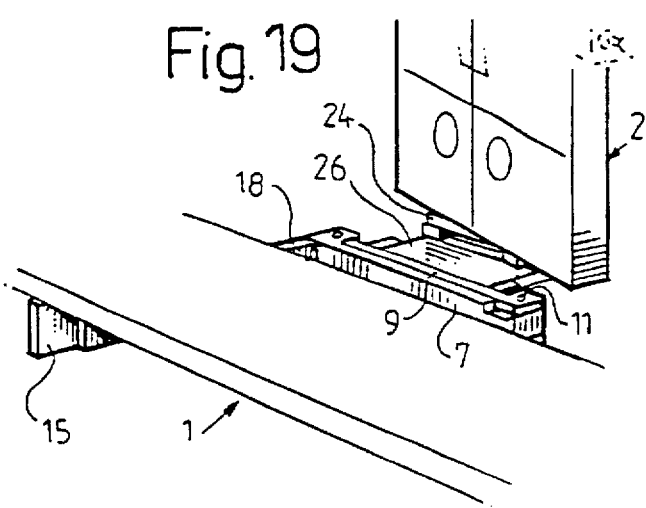
FIG. 19 is a perspective view showing that the receptor unit can be swung about a vertical axle relative to its carrying means, so as to enable pictures to be taken with an angled beam path.

FIG. 18 shows the elements 15–19 in an operative position, after having moved the receptor unit 2 in the Y-direction to the other side of the table 1 relative to the position shown in FIG. 17, and after having swung the receptor unit 2 first to a horizontal position about the axle 21, and thereafter to an upwardly swung, vertical position about the axle 10.

When the receptor-unit support element 15 forms part of a carriage which can be moved in the X-direction, the receptor unit can be moved in the X-direction from the position shown in FIG. 18. The beam source will normally accompany this movement of the receptor unit automatically. Movement of the unit in the X-direction and in the Y-direction can be achieved with the aid of appropriate motors (not shown).

As indicated in FIGS. 14–19, the receptor unit 2 may include a unit 28 which carries a joy-stick 27 and which functions to facilitate movement of the receptor unit in different directions. Obviously, the unit 28 may be placed in some other position, for instance on one or both sides of the table or on a table-carried carriage (not shown).

Figure 20:
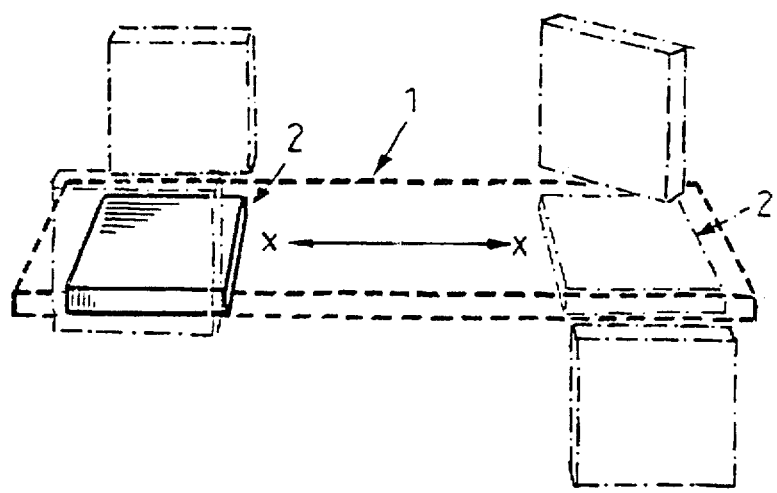
FIG. 20 is a perspective principle view illustrating some of those positions to which the receptor unit can be adjusted by means of the carrying and journalling arrangement shown in FIGS. 12–19.

FIG. 20 is a perspective view illustrating principly the different positions to which a receptor unit 2 can be moved in relation to a patient support table 1 when using the carrier and bearing mechanisms illustrated in FIGS. 12–19. Some of the positions shown by way of example in FIG. 20 correspond to the positions referenced A, C, F in FIGS. 1 and 2. However, FIG. 20 shows a number of further positions which have been made possible because the receptor unit can be moved in the X-direction and also possibly in the Y-direction, and because the receptor unit can also be swung down from a horizontal position and adjusted about a vertical axle for operating with an angle beam path.

Other modifications of the invention are possible within the scope of its basic concept as expressed in the following Claims. For instance, the receptor unit may be accommodated in a frame which carries a table top, for instance a "floating" table top, i.e. a table top that is movable in the X-direction and/or the Y-direction.

The trend towards the development of filmless systems in which images are produced and stored electronically is particularly well served by the inventive method and the inventive patient support table. Because of the complexity of such electronic systems and because of the cost of such systems in which the receptor is connected directly to an evaluating unit, it is of extreme importance that the receptor can be used universally, therewith avoiding loose film cassettes, for instance.

I claim:

1. A method relating to radiation sensing using a beam source which can be adjusted for at least one of horizontal, vertical and angled beam paths and a receptor unit (2) which can be swung out and up from a position beneath a top surface of a table to a vertical position on one side of and parallel with the table comprising the steps of:

(1) swinging the receptor unit (2) to at least one of two alternative positions outside each table side edge; and (2) swinging the receptor unit (2) upwards to a vertical position about a horizontal axle (10);

wherein said receptor unit being swung through the medium of pivot centres (11, 12), has vertical axles in the region of each side edge of the table (1).

2. A method according to claim 1, further comprising the step of:

positioning respective pivot centres (11, 12) in an X-direction, which is parallel to a longitudinal direction of the table, and in a Y-direction, which is parallel to a transverse direction of the table, wherein centering of the beam source in the X-direction will be the same with both horizontal and vertical beam paths.

3. A method according to claim 1, further comprising the step of:

swinging the receptor unit (2) outwardly to at least one of said alternative outwardly and upwardly swung positions to a position in which said unit is perpendicular to the X-direction.

4. A method according to claim 1, further comprising the step of:

(1) moving the receptor unit in a X-direction with corresponding, automatic movement of the beam source; and (2) adjusting said source for horizontal beam path onto the receptor unit subsequent to having swung said unit outward and upward outside a side edge of the table.

5. A method according to claim 1, further comprising the step of:

supporting the receptor unit (2) with the aid of a support element (15) mounted on at least one of a frame structure which is fixed relative to the table, and on a carriage which is movable in a X-direction in relation to said table, wherein the receptor unit can be moved in the Y-direction relative to the element (15).

6. A method according to claim 5, further comprising the step of:

at least one of raising and lowering the receptor unit from an outwardly swung, horizontal position on one side of the table (1) to a vertical position at least one of above and beneath the table, by pivoting said receptor unit about mutually parallel axles (10; 21) located on mutually different levels.

7. A method according to claim 1, further comprising the step of:

pivoting the receptor unit (2) in an outwardly swung and upwardly swung vertical position about a central, vertical axle (22) for operating with an angled beam path.

8. A patient support table equipped with a receptor unit and intended for radiation sensing, wherein the receptor unit (2):

is supported for movement in a X-direction, which is parallel to the longitudinal direction of the table;

is adapted for coaction with a beam source which is movable in the X-direction, a Y-direction, which is parallel to the transverse direction of the table and in a Z-direction;

is capable of being swung about a horizontal axle; and is capable of being swung out and up about a vertical and a horizontal axle from a position beneath a top surface of the table to a position on one side of and parallel with the table; and is carried by arms (7, 9) which are joined together, by a link (8), through the medium of pivot centres (11, 12) having vertical axles in the region of each side edge of the table (1), to enable the receptor unit (2) to be swung out to alterative positions on each side of the table (1) and swung up to a position in which the receptor unit is parallel with the table for operating with a horizontal beam path, this latter movement of the receptor unit being possible by virtue of a horizontal hinge (10) which connects said unit to one (9) of said arms.

9. A table according to claim 8, wherein the receptor unit (2) can be swung from the position for operation with a horizontal beam path to a position perpendicular to the table, through the medium of a vertical axle.

10. A table according to claim 9, wherein the vertical axle constitutes one (11) of said pivot centres (11, 12).

11. A table according to claim 8, wherein the lengths of the arms (7, 9) and the link (8) allow the receptor unit (2) to take a position for operation with a centered beam path without being moved in the X-direction from its original position (position A) beneath a top surface of the table (1), irrespective of from which side the receptor unit is swung outwards and upwards.

12. A table according to claim 8, wherein the receptor unit (1) and its associated arms (7, 9), link (8) and pivot centres (11, 12) are supported by a carriage mounted on the underside of the table (1) and movable in the X-direction.

13. A table according to claim 8, wherein the table top is movable in at least one of the X-direction and the Y-direction, and the receptor unit (1) is mounted in a frame carried by said table top.

14. A table according to claim 12, wherein the carriage includes an element (15) having means (16–19) for guiding movement of a further element (18) journalled to one (7) of the arms (7, 9), wherein the other (9) of said arms carries a block (20) in which a plate (24) carrying the receptor unit (20) is journalled for pivotal movement about a horizontal axle (10).

15. A table according to claim 14, wherein the block (20) has a further axle (21) which is parallel with said horizontal axle (10) and on which the plate supporting said receiver receptor unit is pivotally mounted.

16. A table according to claim 15, wherein the receptor unit (2) is connected to the plate (24) by means of an axle (25) which extends perpendicularly to the plate and about which the receptor unit can be swung for operation with an angled beam path.

17. A table according to claim 8, wherein at least one of the table and the receptor unit includes an operating device, for manoeuvering the linear movement and pivotal movement of the receptor unit (2) in relation to the patient support table.

18. A table according to claim 12, wherein the carriage includes an operating device, for manoeuvering the linear movement and pivotal movement of the receptor unit (2) in relation to the patient support table.

19. A table according to claim 13, wherein the frame includes an operating device, for manoeuvering the linear movement and pivotal movement of the receptor unit (2) in relation to the patient support table.

* * * * *